United States Patent [19]
Webber

[11] Patent Number: 4,909,956
[45] Date of Patent: Mar. 20, 1990

[54] CHLORINE BLEACH COMPOSITIONS WITH REDUCED FABRIC DYE ATTACK

[75] Inventor: Ralph S. Webber, Cheshire, Conn.

[73] Assignee: Olin Corporation, Cheshire, Conn.

[21] Appl. No.: 242,103

[22] Filed: Sep. 9, 1988

[51] Int. Cl.[4] .................... D06L 3/06; C07D 251/00; C07D 251/36

[52] U.S. Cl. .................... 252/187.34; 252/187.33

[58] Field of Search .................... 252/187.34, 187.33

[56] References Cited

U.S. PATENT DOCUMENTS

| | | | |
|---|---|---|---|
| 3,112,274 | 11/1963 | Morgenthaler | 252/187.34 |
| 3,293,188 | 12/1966 | Brown | 252/187.34 X |
| 3,650,961 | 3/1972 | Hudson | 252/99 |
| 4,148,742 | 4/1979 | Crutchfield et al. | 252/187.26 X |
| 4,211,652 | 7/1980 | Thomas | 210/703 |
| 4,279,764 | 7/1981 | Brubaker | 252/187.34 X |
| 4,310,390 | 1/1982 | Bradley et al. | 204/37.1 |
| 4,337,236 | 6/1982 | Sakowski | 252/186.21 X |
| 4,472,205 | 9/1984 | Cortner | 134/27 |
| 4,707,160 | 11/1987 | Chun et al. | 8/101 |
| 4,713,079 | 12/1987 | Chur et al. | 252/186:34 X |
| 4,743,394 | 5/1988 | Kaufmann et al. | 252/90 |

OTHER PUBLICATIONS

1988 Annual Book of ASTM Standards, vol. 15.04, pp. 15–19.

Kirk-Othmer, Encyclopedia of Chemical Technology, 3rd Ed., vol. 13, John Wiley and Sons. p. 1.

*Primary Examiner*—Brooks H. Hunt
*Assistant Examiner*—Virginia B. Caress
*Attorney, Agent, or Firm*—James B. Haglind; Paul Weinstein

[57] ABSTRACT

Chlorine bleaching granules for colored fabrics which minimize fabric dye attach and fabric damage.

This is accomplished in a bleaching granule for preventing dye attack of fabrics during bleaching, the granule comprising an alkali metal chloroisocyanurate, a buffering agent, and a mitigating agent, where the active alkalinity of the granule is from about 0 to about −9.

26 Claims, No Drawings

CHLORINE BLEACH COMPOSITIONS WITH REDUCED FABRIC DYE ATTACK

This invention relates to chlorine bleaching granules for colored fabrics which minimize fabric dye attack and fabric damage.

Chlorine bleaches are known for their ability to economically remove unwanted stains from fabrics. However many fabric dyes are unstable in high concentrations of chlorine bleaching agents and experience a shift in color and/or a loss of color. Further, natural fabrics such as cotton and wool can be damaged by high chlorine concentrations.

To control the release of chlorine from chlorine-containing bleaching agents such as alkali metal dichloroisocyanurates, bleach particles have been coated or encapsulated with a variety of materials.

U.S. Pat. No. 3,112,274, issued Nov. 26, 1963 to J. H. Morgenthaler et al teaches a process for coating particles of polychloroyanurate with inorganic salt. Dry particles of the polychlorocyanurate in a fluidized bed are sprayed with inorganic compounds including sulfates, phosphates, borates, and carbonates, to produce coated particles having a weight ratio of coating material to polychlorocyanurate of 1:3 to 5:1.

In a related process, R. B. Hudson in U.S. Pat. No. 3,650,961, issue Mar. 21, 1972, teaches spraying an aqueous slurry of core particles of a chlorocyanurate into a fluidized bed of hydratable, particulate inorganic salts.

More recently, hard spherical bleaching particles were formed of an agglomerated mixture containing an alkali metal dichloroisocyanurate, an alkali metal tripolyphosphate and a binding agent, having a melting point in the range of 85° to 125° F., such as soap or a fatty acid, i.e. lauric acid. The particles produced are encased in the binding agent which, as taught in U.S. Pat. No. 4,707,160, issued Nov. 17, 1987 to W. Chun et al, represents 10 to 30 percent by weight of the particle.

While the above references teach coated bleach formulations which are said to prevent pin holing and other severe attacks to fabrics when used in laundry applications, there is no teaching of preventing or minimizing dye attack under conditions of direct contact with high concentrations of the bleaching particles.

U.S. Pat. No. 4,148,742, issued Apr. 10, 1979 to M. M. Crutchfield e al describes detergent compositions which contain a halogen-containing bleach and which include a bleach damage mitigating amount of trisodium or tripotassium imidobis sulfate. These compositions are stated to be able to remove stains from fabrics using a halogen-containing bleach while minimizing the damage to the fabrics themselves.

Bleaching particles including a dihalohydantoin bleach, a buffer salt, and coated with an organic binding agent are taught in U.S. Pat. No. 4,713,079. The hard spherical bleaching particles from a pH of less than 9.5 when dissolved in water.

Brubaker describes encapsulated bleaches (U.S. Pat. No. 4,279,764, issued July 21, 1981) containing a chlorine bleaching agent, a N-H compound such as sulfamic acid, and anhydratable inorganic salt such as sodium carbonate or sodium sulfate where the encapsulating agent is an alkali metal silicate. The encapsulated bleach particles are stated to provide protection against localized dye attack during bleaching operations.

Hydratable inorganic salts such as sodium carbonate are highly alkaline and if used at all, can only be present in very small concentrations. Similarly, the alkali metal silicate coating is strongly alkaline and is used in low concent otherwise dye attack and fabric damage result.

Now it has been found that dye attack and fabric damage can be effectively prevented or minimized by controlling the active alkalinity of the bleach component.

These and other advantages are accomplished in a bleaching granule which comprises an alkali metal chloroisocyanurate, a buffering agent having an active alkalinity in the range of from about 0 to about +10, and a mitigating agent wherein the active alkalinity of the granule is from about 0 to about −9.

More in detail, the novel composition of the present invention includes as the bleaching agent an alkali metal dichloroisocyanurate. Suitable alkali metal dichloroisocyanurates include, for example, sodium dichloroisocyanurate and hydrates thereof, potassium dichloroisocyanurate and hydrates thereof, and mixtures of these alkali metal dichloroisocyanurates. Any suitable amount of the alkali metal dichloroisocyanurates may be used in the granules. For example, the granules may contain from about 10 to about 90 percent by weight of the alkali metal dichloroisocyanurates.

The second component of the novel composition of the present invention is a buffering agent. Buffering agents are compounds which are water soluble and have a selected active alkalinity. As used in the specification, the active alkalinity (or free alkali) of buffering agents and other components of the bleaching granule is expressed as the percent of $Na_2O$ and may be determined by known methods such as the procedure in section 21 of Method D460-84 of the American Society for Testing Materials.

Suitable buffering agents are those having an active alkalinity in the range of from 0 to about +10. Examples of these buffering agents include dialkali metal phosphates such as disodium or dipotassium phosphate, tetraalkali metal pyrophosphates including tetra sodium or tetra potassium pyrophosphate, alkali metal tripolyphosphates and hydrates thereof, alkali metal bicarbonates, alkali metal tetraborates and hydrates thereof, and mixtures thereof.

Preferred as buffering agents are those alkaline compounds having an alkalinity in the range of from about 0 to about +5. Alkali metal bicarbonates and alkali metal tripolyphosphates are exemplary of the preferred embodiments of the buffering agents.

The novel granular composition of the present invention containing a buffering agent having an active alkalinity in the range of 0 to +5 may include amounts of the buffering agent up to about 90 percent by weight of the granule, and preferably from about 10 to abut 50 percent by weight of the granule.

Where the buffering agent has an active alkalinity in the range of from about +5 to about +10, suitable amounts include those up to about 25 percent by weight of the granule.

Up to about 10percent by weight of the granule may be provided by alkaline compounds having an alkalinity in the range of +10 to about +15 such as liquid alkali metal silicates. Similarly, acidic buffering agents having alkalinities in the range of from about −50 to about 0, for example, mono-alkali metal phosphates such as monosodium phosphate, or organic acids such as citric acid may be incorporated in the granules in small amounts, for example, up to about 5 percent by weight of the granule. Additional components which may be incorporated in the granules include neutral salts such as alkali metal chlorides, alkali metal sulfates, alkali metal stearates or mixtures thereof.

The third component of the novel bleaching granule of the present invention is a mitigating agent which aids in the prevention of fabric dye attack and fabric damage when using alkali metal chloroisocyanurates as bleaching agents. Suitable as mitigating agents in the compositions of the present invention are sulfamic acid and heterocyclic amides including cyanuric acid, succinimide, caprolactam, hydantoin, alkyl-substituted hydantoins and mixtures thereof. These mitigating agents may be used in any suitable amounts. For example, the novel bleaching granules of the present invention may include molar ratios of alkali metal dichlorocyanurate to the mitigating agent of from about 5:1 to about 1:2, and preferably from about 4:1 to about 2:1.

The granular composition of the present invention may be produced in any suitable manner which homogeneously incorporates the alkali metal dichloroisocyanurate and the buffering agent. For example, in one method the dry ingredients are thoroughly mixed and compacted using compacting methods such as tableting, briquetting or chilsonating. The compacted forms are milled or crushed and the granules produced screened to provide particles which suitably dissolve when added to a washing machine or are comparable in size to any detergent compositions with which they may be admixed.

When used, for example, in commercial or home washing machines, the novel bleaching granules of the present invention may be added separately or admixed with detergent compositions containing surfactants, saps, builders, enzymes, and filler materials, among others.

Bleaching granules of this invention having an alkalinity in the range of from about 0 to about −9, preferably from about 0 to about −7, and more preferably from about −1 to about −5, are employed in amounts which provide a wash solution with from about 10 to about 200 parts per million of available chlorine for white fabrics. For colored fabrics, suitable amounts are in the range of from about 10 to about 50 parts per million.

The following examples will more fully illustrate embodiments of the invention without being limited thereby. All parts and percentages referred to herein and in the appended claims are by weight unless otherwise indicated.

EXAMPLES 1-9

Mixtures of sodium dichloroisocyanurate dihydrate, the buffering agent, mitigating agent, and any additional additives were prepared and compacted into tablets. The tablets were crushed, ground and screened to provide bleaching granules having sizes in the range of −16 to +60 mesh (U.S. Sieve).

The granules were mixed with water at 40° C. to form pastes having an available chlorine concentration of 140,000 ppm (Procedure 21, ASTM D460). The pastes were applied to 3"×3" swatches of 100 percent cotton denim which had been dyed indigo and allowed to stand 90 seconds. The swatchss were then rinsed with warm water and allowed to dry. The change in brightness of the treated swatches was measured and CIE (Commission International de l'Eclairage) L*a*b values determined using a Hunterlab ColorQUEST model 1200CQ Spectrocolorimeter coupled to an IBM-XT computer and calibrated to a D65 illuminate and 10° observer angle. The results for bleaching granules providing a minimum color shift and minimum color lightening is given in Table I below.

TABLE I

| | Examples | | | | | | | | |
|---|---|---|---|---|---|---|---|---|---|
| Component (% by wt.) | 1 | 2 | 3 | 4 | 5 | 6 | 7 | 8 | 9 |
| Sodium dichloroiso-cyanurate dihydrate | 50 | 50 | 36.5 | 17.3 | 38.1 | 50 | 50 | 50 | 50 |
| Disodium phosphate | | | | | | | | | |
| Sodium bicarbonate | 30.4 | 30.5 | | 74.1 | | 27.9 | 24.9 | | |
| Sodium tripolyphosphate | | | 45.3 | | 52.4 | | | 15 | 15 |
| Sodium metasilicate | | | | | | | | 10 | 10 |
| Sodium sulfate | | | | | | | | 20.9 | 21.35 |
| 1. Hydantoin | 19.6 | | | | | | | | |
| 2. Dimethyhydantoin | | | | | | | 26.1 | | |
| 3. Sulfamic Acid | | | 18.2 | 8.6 | 9.5 | | | | |
| 4. Caprolactam | | | | | | 22.1 | | | |
| 5. Succinimide | | 19.5 | | | | | | | |
| 6. Cyanuric Acid | | | | | | | | 4.1 | 3.65 |
| Active alkalinity | −6.74 | −5.47 | −4.86 | −2.20 | −1.85 | −1.82 | −0.93 | −0.22 | −0.11 |
| Change in brightness | 3.15 | 2.47 | 0.53 | 0.95 | 2.70 | 2.48 | 2.23 | 5.20 | 1.91 |
| pH | 7.18 | 6.94 | 6.49 | 7.58 | 7.47 | 8.19 | 7.01 | 8.58 | 8.82 |

EXAMPLE 10-17

Bleach granules were prepared using the method of EXAMPLES 1-9. A sample of each bleach granule equivalent to providing 1 gram of available chlorine was placed in the center of a 6"×6" swatch of 100 percent cotton denim which had been dyed indigo. A second 6"×6" swatch was placed on top. The four corners of the lower swatch were folded upwards to form a pouch around the sample. Each pouch was immersed in 600 mls. of water at 40° C. containing 3 grams of a commercially available granular detergent containing phosphates, carbonates, silicates, and anionic surfactants for a period of 90 seconds. The pouch was removed, opened, rinsed with water (40° C.) and dried. The brightness of the bottom fabric was measured using the method of EXAMPLES 1-9. The results are recorded in TABLE II.

Comparative Examples A, B, C, and D

Bleach granules were prepared using the method of EXAMPLES 1-9 in which no buffering agent was incorporated or in which sodium carbonate, having an active alkalinity of 28.7, was used as the buffering agent. Samples of each of these granules were placed in the 100 percent cotton denim swatches using the identical procedure of EXAMPLES 10-17. The results are recorded in TABLE II below.

TABLE II

| Component (% by wt.) | Examples 10 | 11 | 12 | 13 | 14 | 15 | 16 | 17 | Comparative Examples A* | B | C | D |
|---|---|---|---|---|---|---|---|---|---|---|---|---|
| Sodium dichloroiso-cyanurate dihydrate | 50 | 50 | 50 | 50 | 50 | 50 | 50 | 50 | 75 | 50 | 50 | 17.3 |
| Citric acid | 5 | | | | | | | | | | | |
| Disodium phosphate | | 25 | | | | | | | | | | |
| Sodium bicarbonate | 20 | | 30.5 | 24.5 | 27.9 | 24.9 | | 48.17 | | 9.5 | 5 | |
| Sodium tripolyphosphate | | | | | | | 15 | | | | | |
| Sodium carbonate | | | | | | | | | | 21.5 | 20 | 74.1 |
| Sodium hydrous silicate | | | | | | | 10 | | | | | |
| Sodium sulfate | | | | | | | 20.92 | | | | | |
| Sodium stearate | | | 0.5 | 0.5 | | | | | | | | |
| 1. Dimethyhydantoin | | | | | | 26.1 | | | | | | |
| 2. Sulfamic Acid | | | 19 | | | 19 | | | | | | 8.6 |
| 3. Caprolactam | | | | | 22.1 | | | | | | | |
| 4. Succinimide | | | | | | | | | | | | |
| 5. Cyanuric Acid | 25 | 25 | 25 | | | | 4.08 | 1.83 | 25 | 19 | 25 | |
| Active alkalinity | −8.42 | −7.41 | −6.32 | −5.90 | −1.82 | −0.93 | −0.20 | −0.20 | −6.22 | −0.34 | −0.33 | 18.30 |
| Change in brightness | 0.79 | 2.44 | 0.27 | 2.65 | 12.57 | 6.97 | 5.62 | 11.11 | 30.21 | 25.72 | 28.31 | 27.50 |

*No Buffer

What is claimed is:

1. A bleaching granule which comprises an alkali metal dichloroisocyanurate, a buffering agent having an active alkalinity in the range of from about 0 to about +10, and a mitigating agent wherein the active alkalinity of the granule is from about 0 to about −9.

2. The bleaching granule of claim 1 in which the mitigating agent is sulfamic acid, a heterocyclic amide compound, and mixtures thereof.

3. The bleaching granule of claim 1 in which the buffering agent is selected from the group consisting of dialkali metal phosphates, tetraalkali metal pyrophosphates, alkali metal tripolyphosphates and hydrates thereof, alkali metal bicarbonates, alkali metal tetraborates and hydrates thereof, and mixtures thereof.

4. The bleaching granule of claim 1 in which the alkali metal dichloroisocanurate is present in the granule in amounts of from about 10 to about 90 percent by weight.

5. The bleaching granule of claim 4 in which the alkali metal dichlorocyanurate is sodium dichloroisocyanurate and hydrates thereof.

6. The bleaching granule of claim 5 in which the buffering agent has an active alkalinity in the range of from about 0 to about +5.

7. The bleaching granule of claim 6 in which the buffering agent is present in the granule in amounts up to about 90 percent by weight.

8. The blacking granule of claim 7 in which the molar ratio of alkali metal dichloroisocyanurate to mitigating agent is from about 5:1 to about 1:2.

9. The bleaching granule of claim 8 in which an acidic buffering agent having an active alkalinity of from about −50 to about is present in amounts up to about 5 percent by weight of the granule.

10. The bleaching granule of claim 8 incorporating a neutral salt selected from the group consisting of alkali metal chloride, alkali metal sulfate, alkali metal stearates, and mixtures thereof.

11. The bleaching granule of claim 8 in which the active alkalinity is from about 0 to about −7.

12. The bleaching granule of claim 8 in which the buffering agent is an alkali metal bicarbonate.

13. The bleaching granule of claim 8 in which the buffering agent is an alkali metal tripolyphosphate.

14. The bleaching granule of claim 8 in which the mitigating agent is sulfamic acid.

15. The bleaching granule of claim 8 in which the mitigating agent is a heterocyclic amide compound selected from the group consisting of cyanuric acid, succinimide, caprolactam, hydantoin, alkyl-substituted hydantoins, and mixtures thereof.

16. The bleaching granule of claim 5 in which the buffering agent has an active alkalinity in the range of from about +5 to about +10 and is present in amounts up to about 25 percent by weight of the granule.

17. The bleaching granule of claim 11 in which the molar ratio of buffering agent to mitigating agent is from about 4:1 to about 1:1.

18. The bleaching granule of claim 5 in which liquid alkali metal silicate having an active alkalinity in the range of from about +10 to about +15 is present in amounts up to about 10 percent by weight of the granule.

19. The bleaching granule of claim 10 in which the neutral salt is an alkali metal sulfate.

20. A process for producing bleaching granules having an active alkalinity of about 0 to about +9 which comprises:

(a) blending particles of an alkali metal dichloroisocyanurate, a buffering agent having an active alkalinity in the range of from about 0 to about +10, and a mitigating agent to form a homogeneous mixture, (b) compacting the homogeneous mixture to provide compacted forms, and (c) crushing the compacted forms to produce granules.

21. The process of claim 20 in which the compacting is selected from the group consisting of tabletting, briquetting or chilsonating.

22. The bleaching granule of claim 12 in which the mitigating agent is sulfamic acid.

23. The bleaching granule of claim 12 in which the mitigating agent is a heterocyclic amide compound selected from the group consisting of cyanuric acid, succinimide, cyanuric acid, caprolactam, hydantoin, alkyl substituted hydantoins, and mixtures thereof.

24. The bleaching granule of claim 12 in which the sodium dichloroisocyanurate and hydrates thereof are present in amount of from about 10 to about 50 percent by weight.

25. The bleaching granule of claim 12 in which the molar ratio of sodium dichloroisocyanurate and hydrates to mitigating agent is from about 4:1 to about 2:1.

26. The bleaching granule of claim 12 in which the alkali metal bicarbonate is sodium bicarbonate.

* * * * *

UNITED STATES PATENT AND TRADEMARK OFFICE
CERTIFICATE OF CORRECTION

PATENT NO. : 4,909,956

DATED : March 20, 1990

INVENTOR(S) : WEBBER

It is certified that error appears in the above—identified patent and that said Letters Patent is hereby corrected as shown below:

Column 5, line 39, please delete "dichloroisocanurate" and insert ---dichloroisocyanurate--- in its place.

Column 5, line 51, please delete "blacking" and insert ---bleaching--- in its place.

Column 5, line 56, after "about" and before "is" please insert ---0---.

Signed and Sealed this

Twenty-fourth Day of December, 1991

*Attest:*

HARRY F. MANBECK, JR.

*Attesting Officer* *Commissioner of Patents and Trademarks*